(12) United States Patent
Young et al.

(10) Patent No.: US 10,589,085 B2
(45) Date of Patent: Mar. 17, 2020

(54) LEAD FOR BRAIN APPLICATIONS

(71) Applicant: MEDTRONIC BAKKEN RESEARCH CENTER B.V., Maastricht (NL)

(72) Inventors: Edward Willem Albert Young, Maastricht (NL); Egbertus Johannes Maria Bakker, Wijk en aalburg (NL)

(73) Assignee: Medtronic Bakken Research Center B.V., Maastricht (NL)

(*) Notice: Subject to any disclaimer, the term of this patent is extended or adjusted under 35 U.S.C. 154(b) by 161 days.

(21) Appl. No.: 14/377,498

(22) PCT Filed: Feb. 5, 2013

(86) PCT No.: PCT/EP2013/052245
§ 371 (c)(1),
(2) Date: Aug. 7, 2014

(87) PCT Pub. No.: WO2013/117547
PCT Pub. Date: Aug. 15, 2013

(65) Prior Publication Data
US 2015/0246218 A1    Sep. 3, 2015

Related U.S. Application Data

(60) Provisional application No. 61/596,249, filed on Feb. 8, 2012.

(30) Foreign Application Priority Data

Feb. 8, 2012    (EP) ..................................... 12154366

(51) Int. Cl.
*A61N 1/05*    (2006.01)
*A61N 1/08*    (2006.01)
*A61N 1/36*    (2006.01)

(52) U.S. Cl.
CPC ............ *A61N 1/0534* (2013.01); *A61N 1/08* (2013.01); *A61N 1/3605* (2013.01)

(58) Field of Classification Search
CPC ........................... A61N 1/0541; A61N 1/0534
See application file for complete search history.

(56) References Cited

U.S. PATENT DOCUMENTS 5,555,888 A * 9/1996 Brewer ................ A61N 1/3702
600/515
2004/0147992 A1* 7/2004 Bluger et al. ................. 607/116
(Continued)

FOREIGN PATENT DOCUMENTS

EP    1790380 B1    5/2009
EP    2626108 A1    8/2013
(Continued)

OTHER PUBLICATIONS

European Patent Office, International Search Report of PCT/EP2013/052245, dated Jul. 18, 2013, WIPO, 3 pages.
(Continued)

*Primary Examiner* — Carl H Layno
*Assistant Examiner* — Jennifer Ghand
(74) *Attorney, Agent, or Firm* — Shumaker & Sieffert, P.A.

(57) ABSTRACT

A lead for brain applications, comprises at least one distal section and at least one electrode, whereby the at least one electrode is arranged in the distal section and whereby the at least one electrode is connected directly and/or indirectly with at least one first connecting trace and at least one second connecting trace. Furthermore, in some examples, the lead relates to a deep brain stimulation (DBS) system.

21 Claims, 5 Drawing Sheets

(56) References Cited

U.S. PATENT DOCUMENTS

| | | | |
|---|---|---|---|
| 2006/0276866 A1* | 12/2006 | McCreery | 607/116 |
| 2007/0123765 A1 | 5/2007 | Hetke et al. | |
| 2008/0255439 A1 | 10/2008 | Tang et al. | |
| 2010/0130844 A1* | 5/2010 | Williams et al. | 600/378 |
| 2011/0301665 A1* | 12/2011 | Mercanzini et al. | 607/45 |
| 2011/0313270 A1* | 12/2011 | Pereira Neves et al. | 600/378 |
| 2013/0085361 A1* | 4/2013 | Mercanzini | A61B 5/04001 600/377 |

FOREIGN PATENT DOCUMENTS

| | | |
|---|---|---|
| WO | 2010055421 A1 | 5/2010 |
| WO | 2011046665 A1 | 4/2011 |
| WO | 2011121089 A1 | 10/2011 |

OTHER PUBLICATIONS

International Preliminary Report on Patentability from International Application No. PCT/EP2013/052245, dated Aug. 21, 2014, 5 pp.
International Search Report and Written Opinion of International Application No. PCT/EP2013/052245, dated Aug. 8, 2014, 3 pp.
Search Report from counterpart European Application No. 12154366.4, dated Apr. 2, 2012, 6 pp.

* cited by examiner

US 10,589,085 B2

LEAD FOR BRAIN APPLICATIONS

CROSS REFERENCE TO RELATED APPLICATIONS

This application is an United States National Phase of International Patent Application PCT/EP2013/052245, entitled "A Lead for Brain Applications," filed Feb. 5, 2013, which claims priority to European Patent Application No. 12 154 366.4, entitled "A Lead for Brain Applications," filed Feb. 8, 2012, and claims priority to U.S. Provisional Application No. 61/596,249, entitled "A Lead for Brain Applications," filed Feb. 8, 2012, the entire contents of each of which are hereby incorporated by reference in their entirety for all purposes.

TECHNICAL FIELD

The present invention relates to a lead for brain applications and to a deep brain stimulation (DBS) system.

BACKGROUND AND SUMMARY

Implantable neurostimulation devices have been used in the past 10 years to treat acute or chronic neurological conditions. Deep brain stimulation (DBS), the mild electrical stimulation of sub-cortical structures, belongs to this category of implantable devices, and has been shown to be therapeutically effective for Parkinson's disease, dystonia, and tremor. New applications of DBS in the domain of psychiatric disorders (e. g. obsessive compulsive disorder, depression) are being researched and show promising results. In existing systems, the leads are connected to an implantable current pulse generator.

Currently, lead systems are under development with more, smaller electrodes in a technology based on thin film manufacturing. These leads will have multiple electrode areas and will enhance the precision to address the appropriate target in the brain and relax the specification of positioning. Meanwhile, undesired side effects due to undesired stimulation of neighbouring areas can be minimized.

Probes that are based on thin film manufacturing are disclosed, e.g., by US 2008/0255439 A1, and have been used in research products in animal studies.

These novel systems consist of a lead made from a thin film based on thin technology. The thin films are assembled on a core material with a cylindrical shape to form a lead. Such a probe is disclosed by US 2007/0123765 A1, which is showing a modular multichannel microelectrode array and methods of making the same.

As the thin film wires and traces for the lead are relatively thin and long in these leads, the electrical resistance gives rise to substantial differences between the driving voltage at the current source and the driving voltage at the distal end. The current pulse can be well controlled though, and as such, the potential at the distal-end is kept within safe limits. However, there is no active voltage control of the potential at the distal end of the lead. For therapeutic applications that require potential control at the distal end, active voltage monitoring at the distal end is required. For safety reasons, voltage monitoring can be beneficial too. Sensing near the electrode can be also beneficial to create an active feedback loop to compensate for pulse to pulse variation between various drivers in the electronic circuit.

It is therefore an object of the present invention to provide a lead for brain applications and a deep brain stimulation system having improved properties, in particular that a voltage monitoring at the distal end of a probe of a brain stimulation system can be conducted.

Accordingly, a lead for brain applications comprises at least one distal section and at least one electrode, whereby the at least one electrode is arranged in the distal section and whereby the at least one electrode is connected directly and/or indirectly with at least one first connecting trace and at least one second connecting trace.

The at least one electrode may be connected directly and/or indirectly in close vicinity of the electrode area with at least one first connecting trace and at least one second connecting trace.

The lead may be a component of a Deep Brain Stimulation probe. The electrodes can be connected to electronic means to provide the pulses and measure signals at the proximal end of such a DBS probe, whereby the electronic means are arranged outside of the brain. Alternatively, the electronic means can be integrated into the probe, in close vicinity of the distal end of the probe and thus the electronic means are arranged inside of the brain.

Thereby, the advantage may be achieved that one connecting trace can be used for, e.g., power supply, and one connecting trace can be used for, e.g., voltage monitoring. The lead for brain applications can be a lead having a thin film based probe design. The brain applications can be, e.g., deep brain stimulation (DBS). Thus, especially the further advantage may be achieved that, e.g., voltage monitoring at the distal end at the location of the stimulation electrode is enabled.

Additionally, it is possible that the first connecting trace is configured such that electrical power can be supplied to the electrode.

Preferably, it is possible that the second connecting trace is configured such that a voltage monitoring of the electrode can be conducted.

In a further preferable embodiment it is possible that the first connecting trace and the second connecting trace are directly connected to the electrode, whereby preferably the first connecting trace and the second connecting trace are directly connected from the proximal end of the lead to the electrode.

Further preferably, it is possible that the first connecting trace is directly connected to the electrode and the second connecting trace is indirectly connected to the electrode.

Especially, the second connecting trace may be connected to the first connecting trace at a connecting point, which is arranged adjacent to the electrode. In particular, the second connecting trace does not necessarily need a connection to the electrode area itself. A design with connection in proximity of the electrode can be used also, which is, e.g., preferred when several electrodes are to be arranged with high density.

The lead may comprise a plurality of electrodes. E.g., several electrodes or all electrodes can be configured such that the electrodes are capable of providing electrical stimulation to the tissue and each of the electrodes is capable of detecting electrical signals. Thereby, the advantage is achieved that a tailor-made stimulation can be conducted by the probe which is equipped with a plurality of electrodes and that thereby the brain tissue to be stimulated can be stimulated with high accuracy. Additionally, the advantage is achieved that also electrical signals can be determined and that this determination process can be done with high accuracy. The electrodes may be arranged in a predetermined geometrical manner forming an array on the probe and that the probe may be implanted at a certain position in a target area of the brain. Due to the fact that the electrodes are arranged in a predetermined geometrical manner a correlation of signals received from the target region and the arrangement of the electrodes can be generated and the necessary electrodes for an optimal neurostimulation treatment can be selected. Advantageously, the target area may then be stimulated with high accuracy, since the array electrodes allows a precise and specific stimulation of the target area.

Preferably, it is possible that the lead is a lead with a thin film and/or whereby the first connecting trace and the second connecting trace are a thin film structure and/or are a part of a thin film structure. Common thin film technologies may be used to manufacture the thin film for the lead, e.g., chemical deposition methods like plating, chemical vapour deposition (CVD), or chemical solution deposition (CSD), etc., physical deposition methods like sputtering, pulsed laser deposition, cathodic arc deposition, or electrohydrodynamic deposition, etc., or other deposition methods like molecular beam epitaxy (MBE) or topotaxy, etc. These methods may be used, in combination with thin film structuring methods, such as photolithography and etching.

Further preferably, the thin film structure may comprise and/or may be connectable to at least one controlling means, whereby the controlling means is configured such that a voltage monitoring can be conducted in connection with the second connecting trace.

Additionally, it is possible that the first connecting traces are arranged in a separate first level and that the second connecting traces are arranged in a separate second level of the thin film structure. It is possible that the traces are embedded in a biocompatible polymer, which can include, e.g., parylene.

In a further preferred embodiment it is possible that the level of the first connecting traces has a first thickness and that the level of the second connecting traces has a second thickness, whereby the thickness of the level of the first connecting traces is thicker than the thickness of level of the second connecting traces. In particular, it is not necessary that the traces have to be manufactured next to each other. The second connecting traces can be manufactured in a separate metal layer or a separate layer level. The metal in the level that is used for the voltage sensing traces can be chosen relatively thin, because the resistivity of the track can be relatively high, especially due to the fact that the second connecting traces may be used for the voltage monitoring only. Voltage monitoring will not be compromised by high resistance in the track as it can be performed with high impedance measuring systems.

Preferably, in a possible embodiment of the deep brain stimulation system the deep brain stimulation system comprises at least one controlling means and/or is connectable to at least one controlling means, whereby the controlling means is configured such that a voltage monitoring can be conducted in connection with the second connecting trace. Advantageously, voltage monitoring can be used to enhance the safety of a DBS system.

It is furthermore possible that the controlling means is configured such that the current, especially the electrical power supplied by the first connecting trace, can be switched off or limited when a safety compliance limit is reached.

Additionally, it is possible that the controlling means is configured such that the voltage applied to the at least one electrode can be determined and controlled and/or that the controlling means is configured such that resistance differences in the first connecting traces and/or resistance differences in the second connecting traces can be electronically corrected. Also, differences in the electronic means, respectively the electronic unit, can be corrected, for example.

Further preferably, it is possible that the controlling means is configured such that changes of the at least one electrode in the brain after implantation can be measured and that the driving of the electrode can be adjusted accordingly.

BRIEF DESCRIPTION OF THE FIGURES

Further details and advantages of the present invention shall be described hereinafter with respect to the drawings.

DETAILED DESCRIPTION

Figure 1:
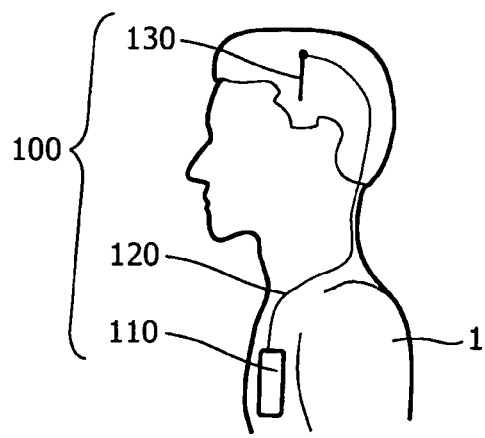
FIG. 1 shows a schematic drawing of a neurostimulation system for deep brain stimulation (DBS).

A possible embodiment of a neurostimulation system 100 for deep brain stimulation (DBS) is shown in FIG. 1 (also referred to as a DBS system or probe system). The neurostimulation system 100 comprises at least a controller 110 that may be surgically implanted in the chest region of a patient 1, typically below the clavicle or in the abdominal region of a patient 1. The controller 110 can be adapted to supply the necessary voltage pulses. The typical DBS system 100 may further include an extension wire 120 connected to the controller 110 and running subcutaneously to the skull, preferably along the neck, where it terminates in a connector. A DBS lead arrangement (also referred to as a probe 130) may be implanted in the brain tissue, e.g., through a burr-hole in the skull.

Figure 2:
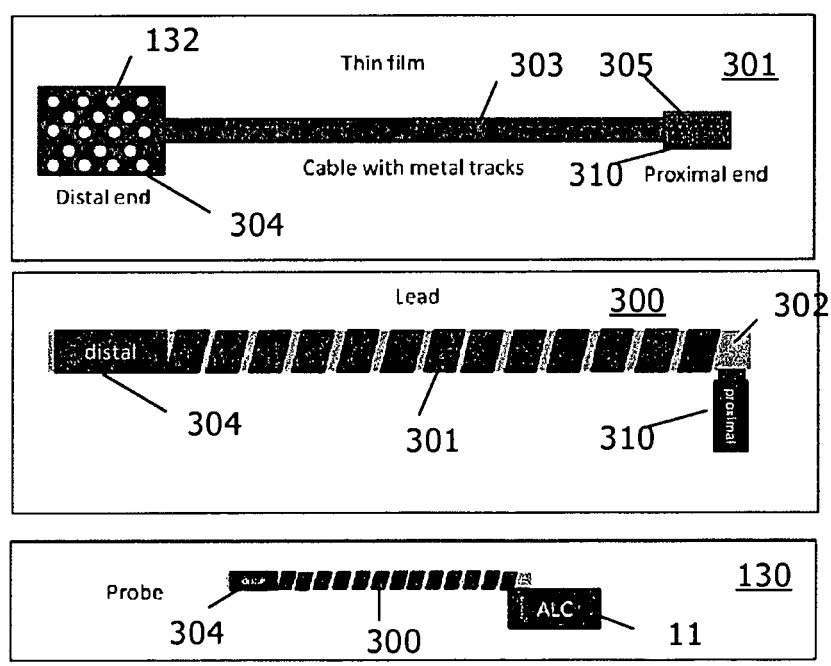
FIG. 2 shows a further schematic drawing of a probe neurostimulation system for deep brain stimulation (DBS) and its components.

FIG. 2 further illustrates a typical architecture for a Deep Brain Stimulation probe 130 that comprises a DBS lead 300 and an Advanced Lead Connector element 11 comprising electronic means to address electrodes 132 on the distal end 304 of the DBS lead 300. The lead 300 comprises a carrier 302 for a thin film 301, said carrier 302 providing the mechanical configuration of the DBS lead 300 and the thin film 301. The thin film 301 may include at least one electrically conductive layer, preferably made of a biocompatible material. The thin film 301 is assembled to the carrier 302 and further processed to constitute the lead element 300.

The thin film 301 for a lead is preferably formed by a thin film product having a distal end 304, a cable 303 with metal tracks and a proximal end 310. The proximal end 310 of the thin film 301 on the lead 300 is electrically connected to the Advanced Lead Connector element 11. The Advanced Lead Connector element 11 comprises the switch matrix of the DBS steering electronics. The distal end 304 comprises the electrodes 132 for the brain stimulation. The proximal end 310 comprises the interconnect contacts 305 for each metal line in the cable 303. The cable 303 comprises of metal lines (not shown) to connect each distal electrodes 132 to a designated proximal contact 305.

Figure 3:
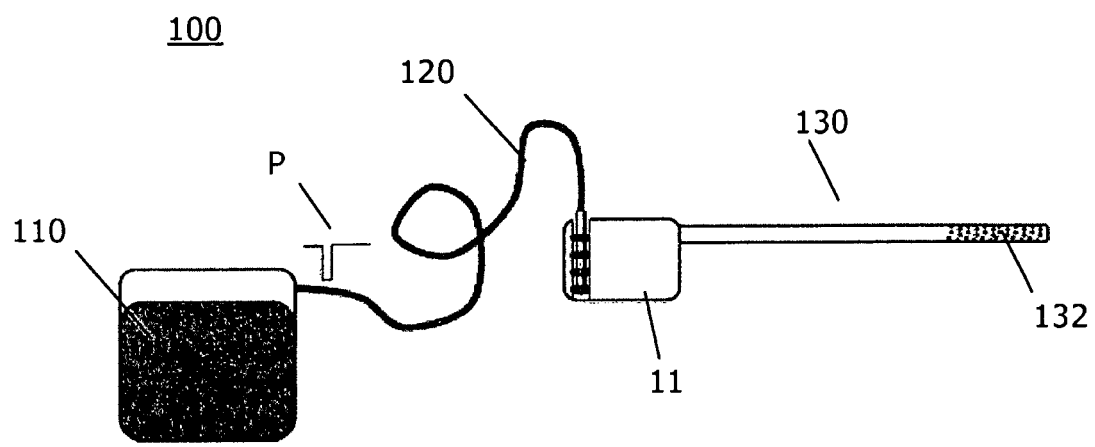
FIG. 3 shows a schematic drawing of a probe system according to the present invention.

FIG. 3 shows schematically and in greater detail an embodiment of a probe system 100 for brain applications, here for neurostimulation and/or neurorecording as a deep brain stimulation system 100 as shown in FIGS. 1 and 2. The probe system 100 comprises at least one probe 130 for brain applications with stimulation and/or recording electrodes 132, whereby, e.g., 64 electrodes 132 can be provided on outer body surface at the distal end of the probe 130. By means of the extension wire 120, pulses P supplied by controller 110 can be transmitted to the Advanced Lead Connector element 11. The controller 110 can be an implantable pulse generator (IPG) 110.

Figure 4:
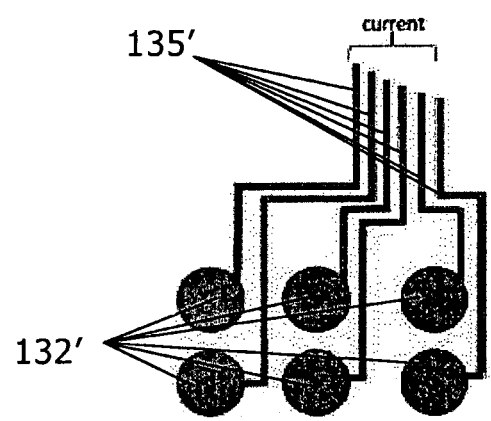
FIG. 4 shows a schematic drawing of electrodes of a lead of a neurostimulation system for deep brain stimulation (DBS).
Figure 5:
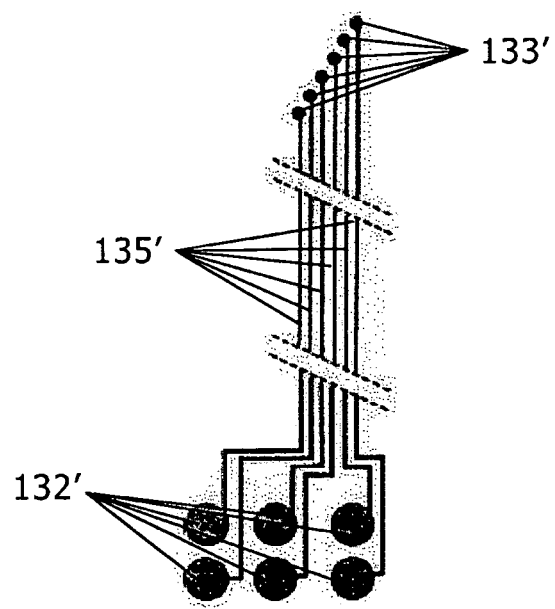
FIG. 5 shows a further schematic drawing of electrodes of a lead of a neurostimulation system for deep brain stimulation (DBS).

FIG. 4 shows a schematic drawing of electrodes on a thin film for a lead of a neurostimulation system for deep brain stimulation (DBS). In such a conventional thin film for a lead design, the distal end electrodes that will be positioned in the brain are connected to electronics outside of the brain. A representation of the distal end of the probe carrying the electrodes 132' is given in FIG. 1. Each electrode has one separate trace connection 135'. The traces 132' lead to the connectors 133' in the proximal end, which is shown in FIGS. 4 and 5. Due to the fact that the traces 132' are relatively long and the films are thin, the resistance in the track can be quite high and can range up to several kOhm depending on the length, track width, and technology.

Figure 6:
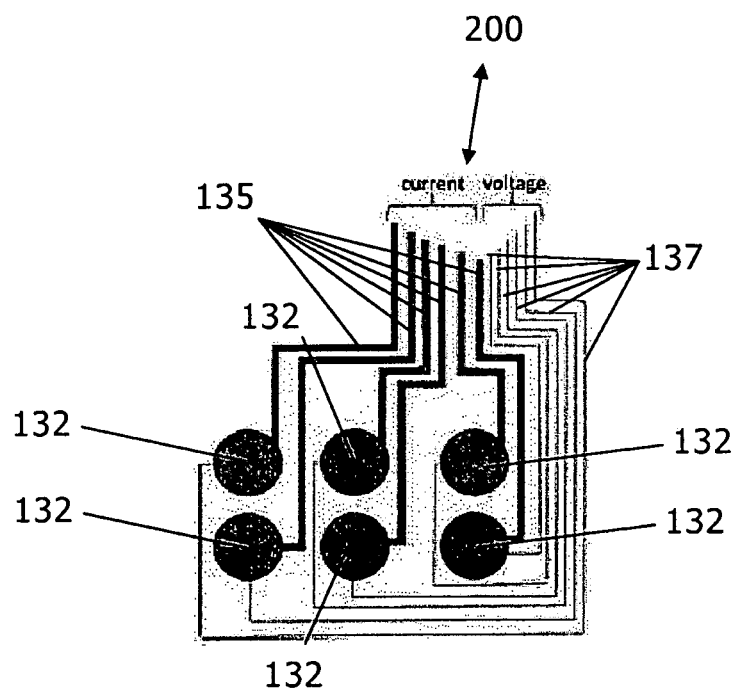
FIG. 6 shows a further schematic drawing of electrodes of a lead of a neurostimulation system for deep brain stimulation (DBS) according to the present invention in a first embodiment.

According to the present invention, the probe 130 for brain applications as shown in FIGS. 1 and 2, comprises at least one distal section and several electrodes 132, whereby the electrodes 132 are arranged in the distal section and whereby the electrodes 132 may be connected directly with first connecting traces 135 and second connecting traces 137, likewise the embodiment shown in FIG. 6.

Each electrode 132 has a first connecting trace 135 and a second connecting trace 137. Each first connecting trace 135 is used for providing current (e.g., electrical power) respectively to the respective electrode 132. Each second connecting trace 137 is used for measuring the voltage, i.e., voltage monitoring and status check of the respective electrode 132.

Voltage monitoring can be used to enhance the safety of a DBS system. The electronics can be programmed to switch off the current when a safety compliance limit is reached. Voltage monitoring enables active voltage control that can be used to control voltage of the electrodes 132 rather than current. This enables novel therapeutic use of the electrodes 132.

Voltage monitoring can be applied to electronically correct for resistance differences, e.g., in the traces 135. It can be part of a charge balancing control system. Furthermore, it can be applied as input for a background diagnostic system. The extra monitoring facilitates the development of an enhanced current steering control mechanism.

The traces 137 to measure the voltage can be very narrow, i.e., high ohmic. By using voltage sensing the line does not carry any current during (high impedance) voltage measurement. As result of this, area use on the thin film can be small.

It is beneficial for the device to avoid routing of electrode connection track and the voltage monitoring track in close vicinity (e.g., neighbouring tracks). This limits the cross-talk as a result of capacitive coupling.

Next to the traces 135 for the electrode powering, (voltage) probe lines 137 are designed in the lay-out. A separate trace 137 can be designed next to each power line trace 135. Alternative routings can be also applied, e.g., such as voltage line traces 137 next to each other (see FIG. 8).

The electrical connection of the electrodes 132 of the distal ends with two separate traces can be used to monitor the electrode by probing the voltage of the electrode with the second trace, e.g., as in a four point probe measurement. Voltage monitoring can be used to enhance the safety of a DBS system 100. The electronics, i.e., the controller 200 can be programmed to switch off or limit the current when a safety compliance limit is reached.

Voltage monitoring enables active voltage control that can be used to control voltage of the electrodes 132 rather than current. This enables novel therapeutic use of the electrodes 132. Voltage monitoring can be applied to electronically correct for resistance differences in the traces 135. Moreover, voltage control can be used to measure the changes of the electrodes 132 in the brain after implantation and adjust the driving accordingly.

The second connecting trace 137 does not necessarily have to connect to the electrode area itself. A design with connection in proximity of the electrodes 132 can be used too, as shown in the embodiment of FIG. 6. According to this embodiment, the first connecting traces 135 are directly connected to the electrodes 132 and the second connecting traces 137 are indirectly connected to the electrodes 132.

Each second connecting trace 137 is connected to the respective first connecting trace 135 at a connecting point 139, which is arranged adjacent to the respective electrode 132.

The deep brain stimulation system 100 may be connectable to at least one controlling means 200 (see, e.g., FIGS. 6, 7, and 8), which may be arranged outside of the brain, e.g., within the associated controller 110 (see FIG. 1). The controlling means 200 may be configured such that a voltage monitoring can be conducted in connection with the second connecting trace 137.

In particular, the controlling means 200 is configured such that the current, especially the electrical power supplied by the first connecting trace 135, can be switched off or limited when a safety compliance limit is reached.

Furthermore, the controlling means 200 is configured such that the voltage applied to the at least one electrode 132 can be determined and controlled and/or that the controlling means 200 is configured such that resistance differences in the first connecting traces 135 and/or resistance differences in the second connecting traces 137 can be electronically corrected.

Additionally, the controlling means 200 is configured such that changes of the at least one electrode 132 in the brain after acute implantation can be measured and that the driving of the electrode 132 can be adjusted accordingly.

Figure 7:
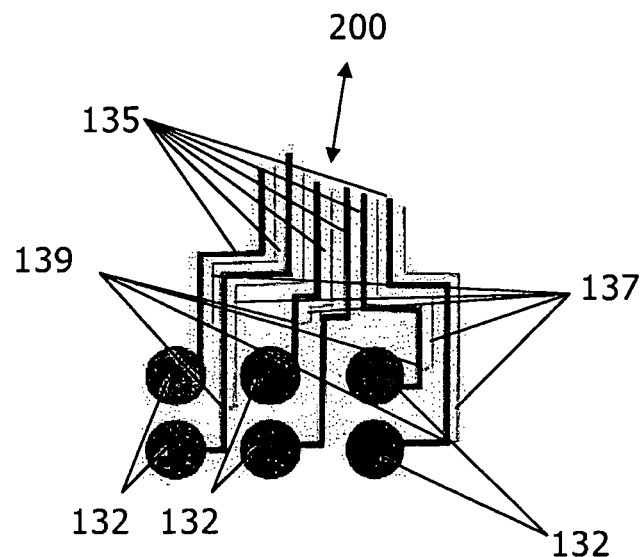
FIG. 7 shows a further schematic drawing of electrodes of a lead of a neurostimulation system for deep brain stimulation (DBS) according to the present invention in a second embodiment.
Figure 8:
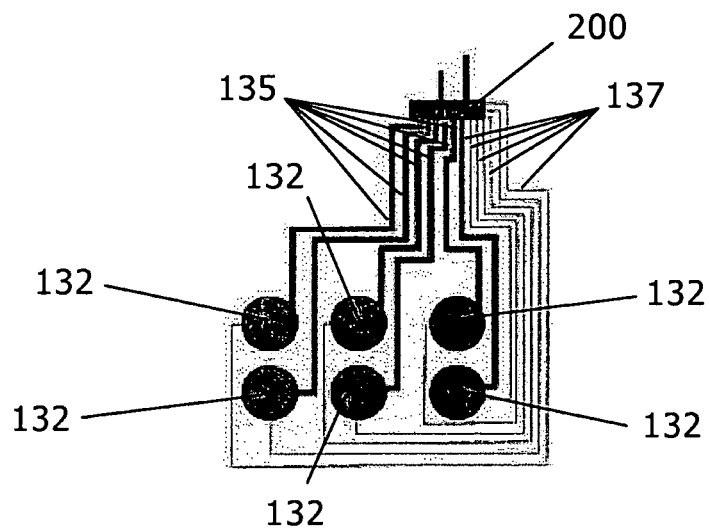
FIG. 8 shows a further schematic drawing of electrodes of a lead of a neurostimulation system for deep brain stimulation (DBS) according to the present invention in a third embodiment.

Though the embodiments shown in FIGS. 6 and 7 relating to application of thin film in neuro-probe applications having electronic means, i.e., the controlling means 200, outside of the brain, an integration of the electronic means, i.e., the controlling means 200, on the thin film is also a possible option, as shown in FIG. 8.

The controlling means 200 of the embodiments shown in FIGS. 6, 7 and 8 comprise at least the same functional features as outlined above. However, functional features can be separated as well between electronic means inside the brain, integrated in the lead near the distal end and electronic means positioned outside of the brain. For instance, voltage measurement can be integrated in the lead and pulse generation is done outside of the brain. Both parts of the electronic means may communicate through (extra) electrical traces on the lead.

Figure 9:
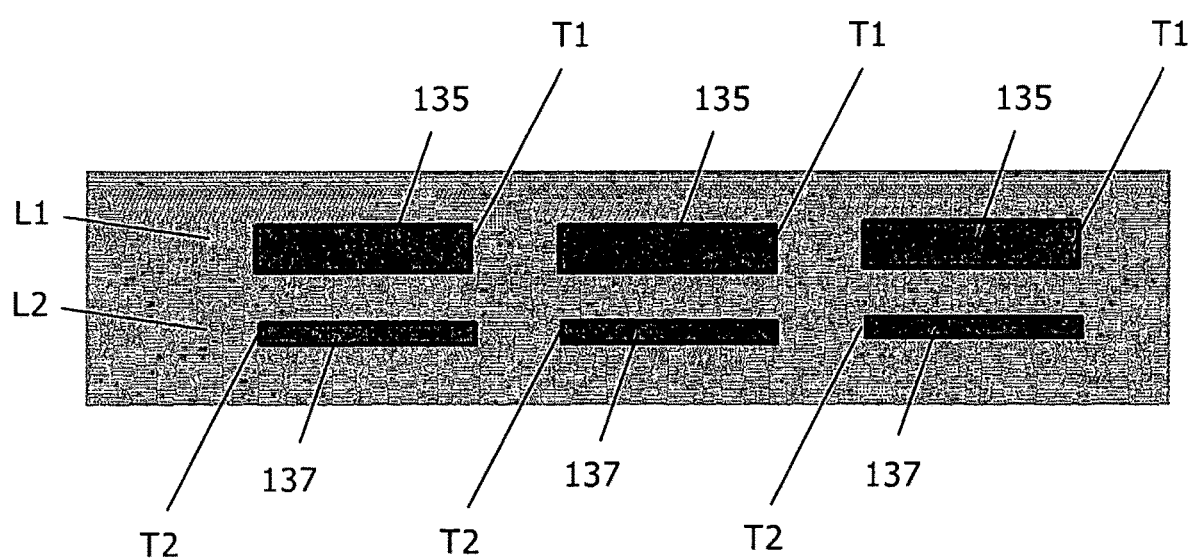
FIG. 9 shows a schematic drawing of the separate layers of the first and second connecting traces of a thin film for a lead according to the present invention.

Furthermore, the traces do not necessarily have to be manufactured next to each other. The traces 135, 137 can be manufactured in a separate metal plane metal, as shown in FIG. 9. The metal in the level that is used for the voltage sensing traces can be chosen relatively thin, because the resistivity of the track can be relatively high. The first connecting traces 135 are arranged in a separate first level L1 and that the second connecting traces 137 are arranged in a separate second level L2 of the thin film structure, which is preferably embedded into a biocompatible polymer such a parylene.

The level of the first connecting traces 135 has a first thickness T1 and the level of the second connecting traces 137 has a second thickness T2, whereby the thickness T1 of the level of the first connecting traces 135 is thicker than the thickness T2 of level of the second connecting traces 137.

The invention claimed is:

1. A deep brain stimulation system comprising:
   a lead comprising at least one distal section, at least one electrode, a first connecting trace, and a second connecting trace, wherein the at least one electrode is arranged in the distal section and wherein the at least one electrode is connected to the first connecting trace and the second connecting trace;
   an electrical power supply, wherein the first connecting trace is configured to supply electrical power from the electrical power supply to the at least one electrode; and
   a controller configured to monitor voltage of the at least one electrode via the second connecting trace, and to control the electrical power supplied to the at least one electrode via the electrical power supply based on the monitored voltage.

2. The system according to claim 1, wherein the first connecting trace and the second connecting trace are directly connected to the at least one electrode.

3. The system according to claim 1, wherein the first connecting trace is directly connected to the at least one electrode and the second connecting trace is indirectly connected to the at least one electrode via the first connecting trace.

4. The system according to claim 3, wherein the second connecting trace is connected to the first connecting trace at a connecting point, which is arranged adjacent to the at least one electrode.

5. The system according to claim 1, wherein the at least one electrode comprises one of a plurality of electrodes arranged in the distal section of the lead.

6. The system according to claim 1, further comprising a thin film structure, wherein the thin film structure comprises the controller.

7. The system according to claim 1, wherein the first connecting trace comprises one of a plurality of first connecting traces and the second connecting trace comprises one of a plurality of second connecting traces, and wherein the plurality of first connecting traces are arranged in a first level of a thin film structure and the plurality of second connecting traces are arranged in a second level of the thin film structure separate from the first level.

8. The system according to claim 7, wherein the first level of the plurality of first connecting traces has a first thickness and the second level of the plurality of second connecting traces has a second thickness, and wherein the first thickness of the first level of the plurality of first connecting traces is thicker than the second thickness of the second level of the plurality of second connecting traces.

9. The system according to claim 1, wherein the controller is configured to control the electrical power supply to limit current delivered to the at least one electrode via the first connecting trace when a safety compliance limit is reached.

10. The system according to claim 9, wherein the current is supplied by the first connecting trace from the electrical power supply to the at least one electrode.

11. The system according to claim 1, wherein the controller is configured to measure changes in resistance of the at least one electrode in a brain after acute implantation and adjust driving of the at least one electrode based on the changes in resistance.

12. The system according to claim 1,
   wherein the at least one electrode comprises one of a plurality of electrodes;
   wherein the first connecting trace comprises one of a plurality of first connecting traces; and
   wherein the second connecting trace comprises one of a plurality of second connecting traces;
   wherein each of the plurality of electrodes is connected to a respective one of the plurality of first connecting traces and a respective one of the plurality of second connecting traces, and
   wherein the controller is configured to
      compare a resistance of each of the plurality of first connecting traces to resistances of each of the other first connecting traces;
      based on the comparison, determine differences in resistances between the plurality of first connecting traces; and
      electronically reduce the differences in resistances between the plurality of first connecting traces.

13. A method comprising:
   delivering electrical stimulation to a brain of a patient via at least one electrode on a lead, the electrical stimulation being provided to the at least one electrode via a first connecting trace of the lead that is coupled to the at least one electrode;
   monitoring a voltage at a distal end of the lead via a second connecting trace of the lead that is coupled to the at least one electrode; and
   controlling electrical power supplied to the at least one electrode via an electrical power supply based on the monitored voltage.

14. The method of claim 13, wherein monitoring the voltage at the distal end of the lead comprises monitoring a voltage of the at least one electrode.

15. The method of claim 13, wherein monitoring the voltage at the distal end of the lead comprises monitoring a voltage of the first connecting trace.

16. The method of claim 13, wherein controlling electrical power supplied to the at least one electrode via an electrical power supply comprises adjusting a current supplied via the first connecting trace.

17. The method of claim 13,
   wherein the at least one electrode comprises one of a plurality of electrodes;
   wherein the first connecting trace comprises one of a plurality of first connecting traces; and wherein the second connecting trace comprises one of a plurality of second connecting traces;

wherein each of the plurality of electrodes is connected to a respective one of the plurality of first connecting traces and a respective one of the plurality of second connecting traces, and wherein the method further comprises:
  comparing a resistance of each of the plurality of first connecting traces to resistances of each of the other first connecting traces;
  determining, based on the comparison, differences in resistances between the plurality of first connecting traces; and
  electronically reducing the differences in resistances between the plurality of first connecting traces.

18. A system comprising:

means for delivering electrical stimulation to a brain of a patient via at least one electrode on a lead, the stimulation signal being provided to the at least one electrode via a first connecting trace of the lead that is coupled to the at least one electrode;

means for monitoring a voltage at a distal end of the lead via a second connecting trace of the lead that is coupled to the at least one electrode; and means for controlling electrical power supplied to the at least one electrode via an electrical power supply based on the monitored voltage, wherein the first connecting trace is configured to supply electrical power from the electrical power supply to the at least one electrode.

19. The system of claim 18, wherein the means for monitoring the voltage at a distal end of the lead comprises means for monitoring a voltage of the at least one electrode.

20. The system of claim 18, wherein the means for monitoring the voltage at a distal end of the lead comprises means for monitoring a voltage of the first connecting trace.

21. The system of claim 18, further comprising means for adjusting a current supplied to the at least one electrode via the electrical power supply via the first connecting trace.

* * * * *